United States Patent [19]

Kokura et al.

[11] 4,426,398

[45] Jan. 17, 1984

[54] FOOD PRODUCT HAVING A MAIN COMPONENT COMPRISING POWDER MADE FROM SOFT SHELL TURTLES AND THE METHOD OF MANUFACTURE THEREFOR

[75] Inventors: Tsunehiko Kokura, Minooshi; Mitsuyori Inoue, Yokohamashi, both of Japan

[73] Assignee: Iwatani Sangyo Kabushiki Kaisha, Osaka, Japan

[21] Appl. No.: 296,533

[22] Filed: Aug. 26, 1981

[30] Foreign Application Priority Data

Dec. 25, 1980 [JP] Japan .................................. 55-186598

[51] Int. Cl.³ .......................... A22C 29/00; A23J 1/04; A23L 1/325
[52] U.S. Cl. ...................................... 426/72; 426/140; 426/285; 426/643; 426/648; 426/657; 426/454; 426/524; 426/805; 426/807
[58] Field of Search ................. 426/643, 444, 534, 385, 426/454, 285, 72, 140, 648, 657, 524

[56] References Cited

U.S. PATENT DOCUMENTS

| | | | |
|---|---|---|---|
| 3,015,611 | 1/1962 | Smedresman | 426/454 X |
| 3,042,531 | 7/1962 | Leal et al. | 426/454 X |
| 3,188,750 | 6/1965 | Davis et al. | 426/385 X |
| 3,490,742 | 1/1970 | Nichols et al. | 426/285 X |
| 3,900,579 | 8/1975 | Masuda et al. | 426/524 X |
| 3,928,639 | 12/1975 | Tangsrud et al. | 426/444 |

FOREIGN PATENT DOCUMENTS 373658  5/1932  United Kingdom ................ 426/444

*Primary Examiner*—Robert A. Yoncoskie
*Attorney, Agent, or Firm*—Schwartz, Jeffery, Schwaab, Mack, Blumenthal & Koch

[57] ABSTRACT

Whole clean, living soft-shelled turtles are frozen in liquid nitrogen. The frozen turtles are crushed and then ground in an atmosphere of nitrogen gas to form a powder. The powder may be mixed with other components, encapsulated or formed into tablets.

20 Claims, No Drawings

FOOD PRODUCT HAVING A MAIN COMPONENT COMPRISING POWDER MADE FROM SOFT SHELL TURTLES AND THE METHOD OF MANUFACTURE THEREFOR

BACKGROUND OF THE INVENTION

1. Field of the Invention

The present invention relates to enriched nutritious food and/or feed comprising a main component of powder made from soft-shelled turtles and the manufacturing method for making the enriched food.

2. Discussion of Related Art

Since ancient times, in China and in Japan, soft-shelled turtles have been served as high quality food which promotes energy and health. These turtles have been used as foodstuffs for physical strength, beauty foods or patients' foods. Moreover, this food contains various nutritious components, described hereinafter, which make it quite useful as well for feed for domestic animals, such as race horses, dogs and so on.

Especially, since race horses are forced to race beyoond the limit of their physical ability, such an enriched nutritious food and/or feed would contribute effectively to controlling their physical condition, promoting their physical strength, and aiding in their fatigue recovery.

However, due to present marketing techniques, soft-shelled turtles must be dealt with as living bodies and/or canned soup. Therefore, this food and/or feed is not available for general use.

Recently, milled paste of living bodies or fermentative food made therefrom have been sold. However, with these foods, difficult problems in quality such as decaying or changing of colors are prevalent. Therefore, even though pure (100%) powder of soft-shelled turtles applicable to various uses has been expected for long time, no high quality product of this type is currently available.

SUMMARY OF THE INVENTION

The purpose of the present invention is to provide enriched nutritious food and/or feed consisting mainly of minute powder made from soft-shelled turtles and also the manufacturing method therefor.

Another object of the present invention is to provide a food which can be taken by itself, or, by adding to and mixing with other foods, can be used as raw material for processing foods.

A further object of the present invention is to provide a food which can be used as domestic animals' feed.

The manufacturing method for producing minute powder of soft-shelled turtles comprises the following procedures.

Living soft-shelled turtles are cleaned without feeding at least for 2 days. After that, in a crushing process, they are immersed in liquid nitrogen and are frozen completely, and the whole frozen living bodies are then crushed into small masses with a coarse crusher.

After the crushing process, the masses are pasteurized by any pasteurizing means, in a pasteurizing process.

After pasteurization, the small masses of soft-shelled turtles are dried well by any drying means in a drying process.

After pasteurizing and drying, in a grinding process, the small masses are frozen with the liquid nitrogen and are ground down into a minute powder in the nitrogen atmosphere at a temperature equal to or below $-50$ degrees centigrade.

However, in an alternate method, the pasteurizing and drying procedures can be executed after the grinding process.

DETAILED DESCRIPTION OF THE PREFERRED EMBODIMENTS

The following descriptions relate to a procedural embodiment of a manufacturing method for producing enriched nutritious food and/or feed consisting mainly of minute powder made from soft-shelled turtles.

First, after cleaning the entire living bodies of soft-shelled turtles without feeding them for at least 2 days, these living turtles are immersed in liquid nitrogen at a temperature of $-196$ degrees centigrade and are frozen completely. Immediately after freezing, the bodies are crushed into small masses having a size of nearly 1 cm by a coarse crusher. When immersed in the liquid nitrogen, the living bodies of soft-shelled turtles turn very brittle because of the low temperature. Thus, the frozen living bodies can be minutely crushed easily and quickly.

It is not practical to crush the bodies without applying liquid nitrogen because a temperature of $-40$ degrees centigrade produced by an ordinary freezing method does not provide the low temperature brittleness essential for the crushing.

Only by applying a super low temperature freezing method using liquid nitrogen can the process be executed.

After crushing, the masses of soft-shelled turtles are sterilized by a high-pressure flash pasteurization. This pasteurization is an indispensable process because soft-shelled turtles contain various kinds of bacterium. Because the primary fat contained in soft-shelled turtles has the characteristic of being oxidized quite easily, before pasteurizing it is preferable to add a given percentage of vitamin E in order to prevent oxidization. After pasteurization, the small masses are dried by an ordinary freeze drying method so that the water content is reduced below 4 percent.

At this stage, the dried masses consist of dark blown solid chunks of bone, shell and meat having a size of about 1 cm, and having a proper flavor for soft-shelled turtles.

The dried masses are then frozen by immersing them in liquid nitrogen at a temperature of $-196$ degrees centigrade, and after that the masses, including all the components, are ground down to a minute powder having a grade equal to or smaller than 200 mesh in an atmosphere of nitrogen gas at a temperature of $-50$ degrees centigrade.

The minute powder formed is a beautiful dark brown color and is a high quality, bacteria free product having a flavor appropriate to soft-shelled turtles.

The liquid nitrogen is used for the following reasons. The dried masses have a primary fat content of over 17 percent, which fat is easily oxidized. Therefore the masses must be ground at a low temperature which is equal to or below $-50$ degrees centigrade.

Also, it is difficult to crush masses of bones and shells completely at a normal temperature. Therefore they have to be crushed at a low temperature so as to be ground uniformly to a minute powder having a grade equal to or smaller than 200 mesh.

However, it is possible to perform the pasteurizing and drying processes after the grinding process.

That is, after freezing and coarsely crushing the soft-shelled turtles into small masses, these masses are ground into a minute powder in a nitrogen atmosphere at a temperature equal to or below −50 degrees centigrade, and after that the powder can be pasteurized and dried.

When the process includes pasteurization, the powder made from the soft-shelled turtles is cooked minute powder of dark brown color, but when blood removal is performed and pasteurization is omitted, a beautiful white raw minute powder can be obtained.

Hereinafter, the description relates to the characteristics of the powder made by the above manufacturing method and preferable embodiments of enriched nutritious food and/or feed consisting mainly of minute powder made from soft-shelled turtles according to the present invention.

The powder contains various useful nutritious components which are not oxidized, and also contains gelatine and fat with no loss by effusion. These components are in minute powder form having a grade equal to or smaller than 200 mesh, and have tastes and flavors appropriate to soft-shelled turtles.

The minute powder is quite convenient to deal with, and is easily blended with various raw materials. Also the powder is very useful as a raw material for processed foods and has a high nutritional value.

The minute powder contains many quality proteins, amino acids, minerals, vitamins and fats containing the same unsaturated fat-acids as that of a plant. Therefore the powder can be used as food and/or feed for men and/or animals.

The general analytical value of the powder is shown in the following table 1.

TABLE 1

| | |
|---|---|
| water (drying at normal pressure) | 2.8% |
| protein (coefficient 6.25) | 53.3% |
| fat (Soxhlet extracting method) | 24.9% |
| fibre | 0.2% |
| mineral | 16.6% |
| sugar | 2.2% |
| calorie per 100 g | 447 cal |

As for the complete hygienic analytic value of the powder, general raw bacteria is below 300 /g, and colon bacillus group is negative, and peroxide value is 26.8 meg/kg.

The powder contains such amino acids as arginine, lysine, leucine, alanine, glycine, proline, glutamic acid, serine, asparaginic acid and other amino acids. The powder also contains such vitamins as retinol, vitamin B1, vitamin B2, vitamin B6, vitamin B12, vitamin E, choline, niacin, folic acid, pantothenic acid, biotin and inositol, and contains such minerals as calcium, kalium, ferrum, zinc and lead.

Thus, the minute powder made from soft-shelled turtles contains as many if not more nutritious components than ordinary medicines for health. And the powder is very valuable as an additional raw material for various kinds of food and/or feed and drinks, and also as an auxiliary nutritious food for seasoning and flavoring, as well as a raw material for medical use.

Hereinafter, the description relates to the most preferable embodiments of the powder as an (1) The first embodiment is the enriched nutritious food and/or feed consisting of pure minute powder made from soft-shelled turtles according to the foregoing manufacturing method. The enriched food and/or feed can be utilized as a nutritious and tonic food and/or feed for the health of men and/or animals (for example, race horses and dogs, etc.), and also as an auxiliary additional food for seasoning and flavoring, as well as an additional raw material for healthy food, drinks and Chinese medicines.

(2) The second embodiment is in the form of enriched nutritious capsules made by the following procedure. First of all, the minute powder in the proportion of 30% to 20% is added to natural vitamn E in the proportion of 30% to 20%. Next, this mixture is mixed into wheat germ oil in the proportion of 50%, and after that the mixture is encapsulated in gelatine capsules.

Hereinbefore, % shows weight percentages, and the reason for adding vitamin E is to prevent oxidizing and also to enrich the food in vitamin E. The reason for mixing with wheat germ oil is to improve the convenience of encapsulating and at the same time to add various vitamins and thereby prevent oxidation and improve the storage life of the product.

The enriched nutritious capsules can be taken by themselves, and also can be utilized as additional food for seasoning and flavoring in cooking.

(3) The third embodiment is in the form of enriched nutritious granules made by the following procedure. First, the following ingredients are mixed: minute powder (40%); lactose (about 46%) as an excipient; pickled-plum powder (about 3%); bone powder (about 2%); sea-tangle powder (abot 2%); others (about 3%) for spice; and ester (about 4%) for decay stimulator. These components are mixed uniformly, and the mixture of powder is added to water and alcohol and kneaded to form a paste. The paste is formed into granules by a granulating machine. The weight percentages given above for the components are given as a percentage of the granule product. If necessary, seasoning may be added.

It is also possible to manufacture tablet products by processing nearly the same mixed paste as described above in a tablet-forming machine.

The foregoing description is set forth for the purpose of describing the present invention in sufficient detail to enable one of ordinary skill in the art to make and use the invention. However, this description is not meant to limit the scope of the invention. Clearly, numerous additions, changes in preparation and other modifications can be made to the invention without departing from the scope thereof, as set forth in the appended claims.

What we claim is:

1. A method of manufacturing powder from soft shell turtles, comprising:
   freezing clean, living soft shell turtles by immersing said soft shell turtles in liquid nitrogen;
   coarsely crushing the frozen soft shell turtles; and
   grinding the crushed soft shell turtles into a powder in an atmosphere of nitrogen gas at a temperature at least as low as −50 degrees centigrade.

2. The method as set forth in claim 1 and further including the steps of pasteurizing the crushed soft shell turtles and drying the pasteurized crushed soft shell turtles.

3. The method as set forth in claim 1 and further including the steps of pasteurizing the ground soft shell turtles and drying the ground pasteurized soft shell turtles.

4. The method as set forth in claim 2 and further including the step of refreezing the dried soft shell turtles at a temperature at least as low as −50 degrees centigrade before grinding the soft shell turtles.

5. The method as set forth in claim 1, wherein the step of freezing further comprises freezing the soft shell turtles to a temperature of about −196 degrees centigrade or lower.

6. The method as set forth in claim 4, wherein the step of refreezing comprises refreezing the dried soft shell turtles in liquid nitrogen at a temperature of about −196 degrees centigrade or less.

7. The method as set forth in claim 1, wherein the frozen soft shell turtles are crushed to a size of about 1 centimeter.

8. The method as set forth in claim 1 or 7, wherein the crushed soft shell turtles are ground to a grade of about 200 mesh or smaller.

9. A food product comprising powder of soft shell turtles made by:
   cleaning living soft shell turtles;
   freezing the living cleaned soft shell turtles by immersing the living cleaned soft shell turtles in liquid nitrogen;
   coarsely crushing the frozen soft shell turtles;
   grinding the coarsely crushed soft shell turtles into a powder in an atmosphere of nitrogen gas at a temperature at least as low as −50 degrees centigrade;
   pasteurizing the ground soft shell turtles; and
   drying the ground pasteurized soft shell turtles to remove moisture.

10. The food product as set forth in claim 9, wherein the liquid nitrogen freezes the cleaned soft shell turtles to a temperature of about −196 degrees centigrade or lower.

11. The food product as set forth in claim 9, wherein the frozen soft shell turtles are crushed to a size of about 1 centimeter.

12. The food product according to claim 9, wherein the crushed soft shell turtles are ground to a grade of about 200 mesh or smaller.

13. The food product as set forth in claim 9 and further including wheat germ oil mixed with said powder of soft shell turtles, and a gelatin capsule enclosing said mixture.

14. The food product as set forth in claim 13 and further including vitamin E mixed with said powder of soft shell turtles and wheat germ oil.

15. The food product as set forth in claim 9 and further including spice and excipient mixed with said powder of soft shell turtles.

16. The food product as set forth in claim 15, wherein said mixture is formed into tablets.

17. A food product comprising powder of soft shell turtles made by:
   cleaning living soft shell turtles;
   freezing the cleaned, living soft shell turtles by immersing the cleaned, living soft shell turtles in liquid nitrogen;
   coarsely crushing the frozen soft shell turtles;
   pasteurizing the crushed soft shell turtles;
   drying the pasteurized, crushed soft shell turtles to remove moisture; and
   grinding the coarsely crushed soft shell turtles into powder in an atmosphere of nitrogen gas at a temperature below at least −50 degrees centigrade.

18. The food product as set forth in claim 17, wherein the dried, ground and pasteurized soft shell turtles are refrozen at a temperature at least as low as −50 degrees centigrade before being ground.

19. The food product as set forth in claim 18, wherein the dried soft shell turtles are refrozen in liquid nitrogen at a temperature of about −196 degrees centigrade or lower.

20. The food product as set forth in claim 17, wherein the cleaned living soft shell turtles are frozen at a temperature of about −196 degrees centigrade.

* * * * *